United States Patent [19]

Cody et al.

[11] Patent Number: 5,759,938
[45] Date of Patent: Jun. 2, 1998

[54] PROCESS FOR PRODUCING ORGANOCLAYS WITH QUATERNARY AMMONIUM COMPOSITIONS MADE USING NON VOLATILE DILUENTS

[75] Inventors: Charles Cody, Robbinsville, N.J.; Barbara Campbell, Bristol, Pa.; Araxi Chiavoni, Trenton; Edward Magauran, Westampton, both of N.J.

[73] Assignee: Rheox, Inc., Hightstown, N.J.

[21] Appl. No.: 820,498

[22] Filed: Mar. 19, 1997

Related U.S. Application Data

[62] Division of Ser. No. 552,452, Nov. 3, 1995, Pat. No. 5,634,969, which is a division of Ser. No. 385,295, Feb. 10, 1995, abandoned.

[51] Int. Cl.$^6$ ............................................. C01B 33/44
[52] U.S. Cl. .................... 502/62; 106/287.17; 501/148
[58] Field of Search ................. 502/62; 106/287.17; 501/148

[56] References Cited

U.S. PATENT DOCUMENTS

| | | | |
|---|---|---|---|
| 4,434,076 | 2/1984 | Mardis et al. | 106/287.17 |
| 4,769,078 | 9/1988 | Tso | 501/148 |
| 4,834,048 | 5/1989 | House et al. | 501/148 |
| 4,876,030 | 10/1989 | Dixon et al. | 106/287.17 |
| 5,334,241 | 8/1994 | Jordan | 501/148 |

*Primary Examiner*—David Brunsman
*Attorney, Agent, or Firm*—Michael J. Cronin

[57] ABSTRACT

Quaternary ammonium compositions are described which are made using diluents including soya bean oil, caster oil, mineral oils, isoparaffin/naphthenic and coconut oil. Such diluents remain as diluents in the final product and generally have a vapor pressure of 1 mm of Hg or less at 25° C., and are liquid at ambient temperature. The quaternary/ammonium diluent compositions have low volatile organic compound emission rates and high flash points, and can be tailored to particular applications. Such applications include use a fabric softeners, cosmetics ingredients, deinking additives, surfactants, and reaction materials in the manufacture of organoclays.

8 Claims, 1 Drawing Sheet

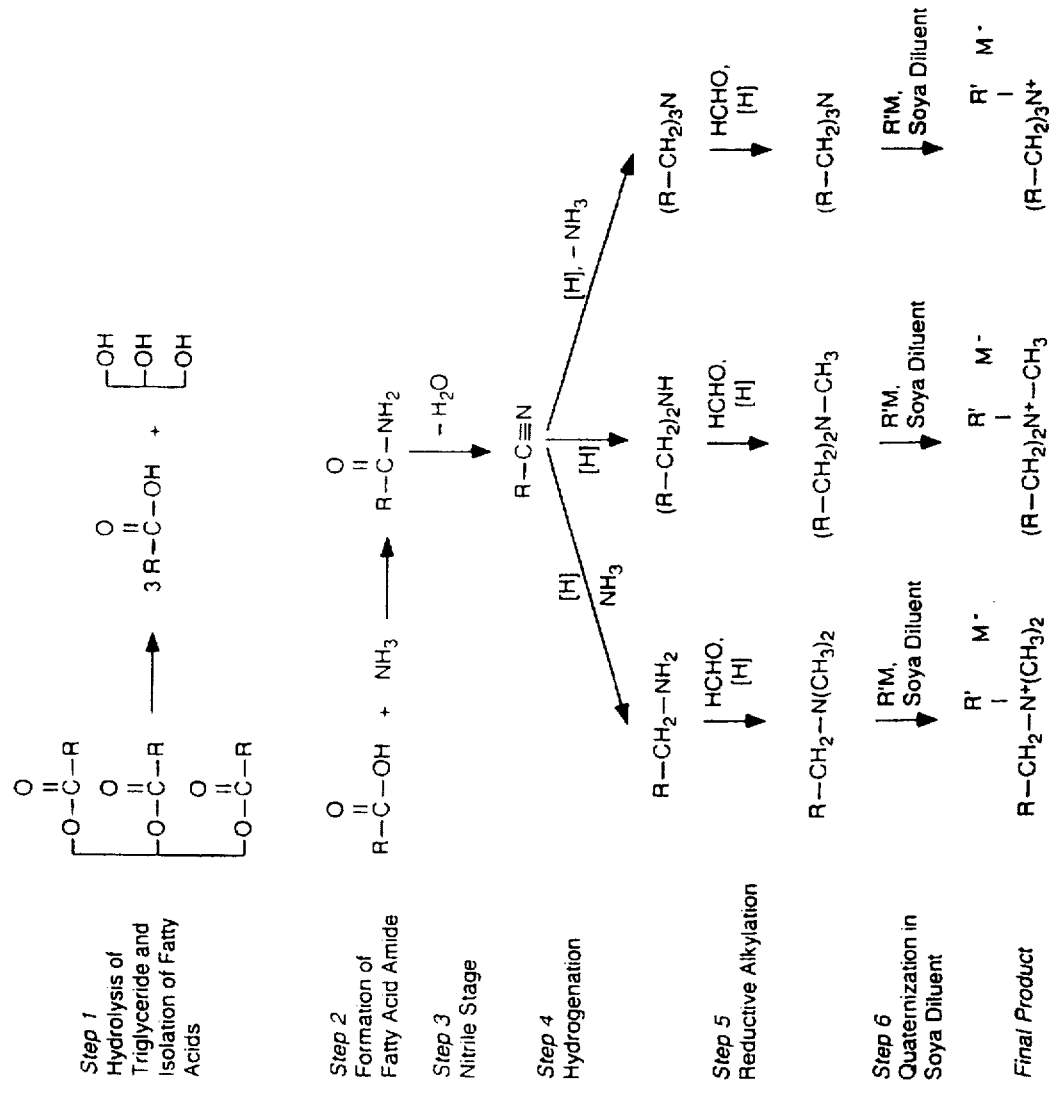

PROCESS FOR PRODUCING ORGANOCLAYS WITH QUATERNARY AMMONIUM COMPOSITIONS MADE USING NON VOLATILE DILUENTS

This is a division of application Ser. No. 08/552,452 filed on Nov. 3, 1995, now U.S. Pat. No. 5,639,969 which application was a divisional application of application Ser. No. 08/385,295, filed Feb. 10, 1995, now abandoned.

BACKGROUND OF THE INVENTION

1. Field of the Invention

Quaternary ammonium salts or "compounds" are tetra-substituted ammonium salts. They have a large number of commercial applications, including uses as ingredients for fabric softeners, as reaction materials in the manufacture of organophilic clays, as cosmetic ingredients, and as bactericidal agents. The chemical reaction processes used to synthesize quaternary ammonium compounds normally require the use of a non-reactive solvent to reduce the viscosity of the amines, particularly tertiary amines, prior to and during quaternization. The solvent most often employed commercially is isopropyl alcohol ("IPA"). Upon completion of the quaternization reaction process, the resulting quaternary ammonium compounds remain in solution, and are commonly sold as quaternary ammonium compositions in such a solvent mixture, or are dried, ground and then sold as relatively solvent-free powders.

In many applications using quaternary ammonium compounds the presence of solvents such as isopropyl alcohol diminishes the desired performance of the quaternary compound and adds environmental and manufacturing hazards due to the isopropyl alcohol's flammability, volatility and toxicity. Drying techniques have been developed which are capable of removing isopropyl alcohol from certain quaternary-solvent mixtures, but are not generally employed, because they add significant manufacturing costs, while failing to remove all of the isopropyl alcohol.

2. Summary of the Invention

The present invention involves the discovery that quaternary ammonium compounds, synthesized using specified diluents, provide improved properties and possess numerous advantages over essentially identical quaternary ammonium compounds quaternized using isopropyl alcohol or other prior art solvents. Quaternary manufacturers employing the new invention, in addition to obtaining superior products, will also obtain the flexibility to utilize specific diluents selected either to promote beneficial effects in the ultimate product from the presence of the novel diluent, or at a minimum, to avoid existing deleterious effects on the systems of quaternary ammonium compound applications caused by IPA contamination. Such use will also lead to improved product handling properties by significantly reducing the flammability, toxicity and environmental hazards associated with quaternary ammonium compounds made and sold with traditional volatile vehicles, and will open new markets to such products. Particularly beneficial uses are in providing ways of making improved organoclays, cosmetic products including shampoos, and fabric softeners, as well as new uses of quaternary ammonium compounds as additives for the deinking of wastepaper pulp and as surfactants for laundry products.

3. Description of the Prior Art

Quaternary Ammonium Compounds

Quaternary ammonium compounds (sometimes abbreviated as "quats") of the type useful in this invention typically are salts of organic cations which have a positive charge localized on a single nitrogen atom and a charge neutralizing anion designated $M^-$.

Quaternary ammonium compounds have the following formula:

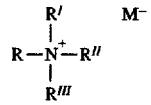

These quaternary ammonium compounds may be described as having four moieties where R is an organic radical and R', R" and R'", the remaining groups attached to the central nitrogen atom, are typically selected from the group consisting of (a) alkyl groups; (b) aralkyl groups which are benzyl and substituted benzyl moieties; (c) aryl groups such as phenyl; (d) beta, gamma-unsaturated groups having six or fewer carbon atoms, (e) hydroxyalkyl groups having 2 to 6 carbon atoms; and (f) hydrogen. The principal groups above are most often derived from naturally occurring fats or oils such as tallow, corn oil, soybean oil, cottonseed oil, castor oil, linseed oil, safflower oil, palm oil, peanut oil and the like. Mixtures of oils are commonly employed. The oil may be of natural sources, or a synthetic version of same, or modifications of a naturally occurring oil using known techniques. A broad listing of the useful components used to make quaternary ammonium compounds ("quats") is described in U.S. Pat. No. 5,336,647.

$M^-$ is an anion which usually is chloride, methyl sulfate, bromide, iodide, hydroxyl, nitrite or acetate. The anion accompanying the organic cation is selected so as not to affect adversely the intended use of the quaternary ammonium compound, and may optionally be selected to impart unique characteristics to the quaternary compound.

Commercially significant quats usually contain at least one residue of a naturally occurring oil, most often derived from beef tallow. In addition to the uses previously mentioned, these quaternary ammonium compounds also find utility as surfactants, anti-static agents, flotation agents, biocides, and, as stated, as reactants in the formation of organically-modified clay rheological control additives for paints, coatings, drilling muds and the like. In addition, poly-quaternary compounds with more than one nitrogen atom have been utilized and are included in the definition of quaternary ammonium compounds.

Processes of Making Quaternary Ammonium Compounds

The manufacture and preparation of quaternary ammonium compounds is achieved by techniques well-known in the art. When preparing a quaternary ammonium salt, one skilled in the art can prepare a dialkyl secondary amine, for example, by the hydrogenation of nitrites, and then form the methyl dialkyl tertiary amine by reductive alkylations using formaldehyde or dimethoxymethane as a source of the methyl radical. A commercial manufacturing process typically involves various stages, including those resulting in the creation of nitrites, primary amines, secondary and tertiary amines, and finally the quaternary compound itself.

The manufacturing process generally involves saturation of fatty acids derived from tallow, or of a commercial natural oil, by hydrogenation as an early step. This has led manufacturers to use the term, "hydrogenated tallow", or "HT", when describing common quaternary ammonium compounds, even those not exclusively derived from tallow fatty acids. Saturated, relatively long-chain hydrocarbon molecules are typically solids or very highly viscous liquids at room temperatures. They may be liquified by heating, but, particularly as the molecular weight of the intermediate products is increased in the course of the manufacturing process, the heat-induced liquification will not compensate for increasing viscosity, which will inhibit subsequent manufacturing steps. Accordingly, the quaternization step typically has been done in a liquid medium in order to solvate and reduce the viscosity of the both the starting material and the reaction products, and to reduce foaming. The medium used for commercial processing has almost universally been isopropyl alcohol (IPA).

Quaternization reactions are typically carried out in the presence of an inorganic alkali-such as sodium bicarbonate, sodium hydroxide, sodium or calcium carbonate—to react with any acid that may be formed as a by-product from the reaction of the alkylating agent (typically an alkyl or aralkyl halide) with labile hydrogen compounds contained within the reaction mixture. Such acidic materials form salts with the amine reactant, deactivating it toward quaternization. Such labile hydrogen compounds include, but are not limited to, primary and secondary amines—typically from incomplete reductive alkylation of the amine in the preceding step—water, and, when an alcoholic diluent is used as the reaction medium, the reaction solvent itself. Thus, while a chemical such as isopropanol will generally serve to accelerate the reaction of the alkylating agent with the amine and the reaction of any acidic by-products with the inorganic alkali, it will also reacts with the alkylating agent to generate unwanted acidic compounds and consumes the alkylating agent.

After manufacture, unless expensive vacuum distillation or freeze drying and grinding processes are later performed to produce a powdered product, the commercial quaternary ammonium compound is then generally sold in IPA solution, with typical activities ranging from 25 to 85 percent quaternary ammonium compound. Customers typically have no commercial use for the IPA either when blending the quat (or similar product) in the customer's process or product, such as fabric softener manufacture, or when using it as a reactant, for example in the manufacture of organoclays. Organoclays are the reaction product of smectite-type clay and quaternary compounds. See for example U.S. Pat. No. 4,105,578. The IPA often is discharged into a sewer leading either to a publicly owned water treatment facility or to a permitted direct discharge, or is volatilized and exhausted to the atmosphere when the organoclay is dried. As an alternative, significant expenses may be incurred for capture and reuse of the IPA from the effluent or pre-atmospheric emissions. As environmental controls on indirect dischargers, direct permitted dischargers, and emitters of volatile organic contaminants ("VOC's") are tightened, the cost of IPA disposal has been increasing at a rate several times that of inflation.

Several prior art references describe the various media, including IPA, which have been used to provide the volatile liquid solvent vehicle for quaternary ammonium compound manufacture. U.S. Pat. No. 2,775,617 describes a process for the preparation of defined quaternary ammonium compounds using animal fat tallow oils as starting ingredients. The patent describes the preparation of quaternary ammonium compounds and more particularly the preparation of tetra-alkylammonium compounds by the alkylation of alkyl secondary amines with alkyl halides. The patent teaches the use of the lower alcohols, particularly n-butanol, as solvent media for the reaction. U.S. Pat. No. 2,644,003 describes the making of quaternary ammonium compounds having very strong bactericidal activity using, as the reaction solvents, benzene, toluene, xylene, acetone, ethyl and butyl acetate. The compounds are useful for the disinfection of human skin, as well as the disinfection of utensils including medical instruments. U.S. Pat. Nos. 2,950,318 and 3,175,008 relate to improved processes for the production of quaternary ammonium compounds employing, as the solvent vehicle, one of the low-boiling alcohols including methanol, ethanol, propanol, isopropanol, butanol, isobutanol, and the like, with the preferred solvent being isopropyl alcohol, together with a minimum amount of water. Upon completion of the reaction, the mixture produced contains the quaternary compound in an aqueous alcoholic solution. While not commercially significant certain quaternary manufacturers have made their products in glycols as the solvent including propylene glycol, hexylene glycol and diethylene glycol.

Relatively recent U.S. Pat. No. 4,857,310 shows the preparation of quaternary ammonium compounds from cosmetic and toiletry compositions from castor oil triglycerides carried out using, in one stage, solvents such as toluene, chloroform and dichloromethane, and in a second stage, the organic vehicle ethanol introduced at an elevated temperature. The resulting product is then dried under vacuum at 80° C. to remove the ethanol.

The media described in the prior art, in the main, involve mostly volatile organic compositions which share a number of properties, the most important of which is the low temperature at which they exhibit a vapor pressure of approximately 1 mm. For example ethanol exhibits a vapor pressure of 1 mm, at a temperature of −31° C. while toluene's temperature is −26.7° C. and methanol's is −44° C. While glycols have vapor pressure-higher temperatures, they present problems of toxicity, odor, flammability and solubility in water systems where the quaternary may be used, that they have not been widely used. Most of the solvents employed in the conventional manufacture of quaternary ammonium compounds can be further characterized as having toxicity, low viscosity, low flash and freezing points. In particular, the vapor pressure of almost all the prior art vehicles substantially exceeds 1 mm of Hg at 25° C.

Quaternary ammonium compounds are usually prepared in complex and expensive stainless-steel or glass-lined equipment. The amine, with or without water, is loaded into the reactor and heated to the proper temperature (usually 80°–100° C.), and an alkylating reagent is added. Quaternization of tertiary amines with alkyl halides is bimolecular. The rate of reaction is influenced by a number of factors, including the nature and quality of the starting materials, the basicity and nucleophilicity of the amine, stearic effects, temperature, reactivity of the halide, and the polarity and other characteristics of the solvent used. Such solvents, in addition to providing liquidity, also assist the reaction by stabilizing the ionic nature of the transition stage of the quaternization reaction.

Uses of Quaternary Ammonium Compounds

The use of quaternary ammonium compounds to make organophilic clays is described in a large number of patents. Illustrative patents which describe such organophilic clays and their use as thickeners and rheological additives include U.S. Pat. No. 4,894,182, 4,450,095 and 4,434,075. Organoclays are the reaction products of smectite clays, including hectorite and bentonite, with one or more quaternary ammonium compounds.

Volume 19 of the *Encyclopedia of Chemical Technology* at pages 529 to 530 describes the various uses of quaternary ammonium compounds as fabric softeners. There are three types of commercial products disclosed: the first is a 4–8 wt % dispersion of quaternary ammonium compound, which is added to the rinse cycle of the washing process by the washing machine user. The second commercial product is a quaternary ammonium compound formulation applied to a nonwoven sheet or a polyurethane foam, which is added with the wet clothes into the dryer by the homemaker. This product formulation contains a transfer agent, usually a fatty-acid ester, which allows the quaternary ammonium compound to transfer from the substrate to the wet clothes. The third type of product is a combined detergent, softener and antistatic formulation containing quaternary ammonium compounds, which allows the introduction of all necessary ingredients into the wash cycle of the washing process. In all cases, the benefits to the user are fabric softening, antistatic properties, ease of ironing, and odor improvement, the latter because of the common addition of perfumes to the formulation. The most widely used, and most effective, quaternary ammonium compounds used for fabric softening purposes are the dimethyl bis[hydrogenated tallow] ammonium chlorides and methyl sulfates ("2M2HT").

Another significant use for quaternary ammonium compounds is in certain cosmetics, particularly for hair treatment. Quaternaries have a high affinity for proteinaceous substrates, and this property makes them useful for hair treatment. They impart antistatic effects, increase hair wetting, improve wet and dry combing, and improve feel and luster. Other cosmetic uses are widely diversified, and the quaternary ammonium compound formulations vary from one cosmetic manufacturer to another, depending on the qualities to be emphasized. In some cases, the solvent with the quaternary ammonium compound is acceptable, while in others it must be removed, for example, by spray drying.

Another important use of quaternary ammonium compounds is in compositions for deinking wastepaper, which is a growing industry both in the United States and throughout Europe. Applicant's assignee in pending U.S. Pat. No. 5,336,372 describes a process for deinking wastepaper in an aqueous flotation process utilizing organoclays formed in situ in the deinking apparatus by the use of quaternary ammonium compounds as deinking chemicals, particularly 2M2HT. U.S. Pat. No. 4,935,096 discloses a method for deinking waste printed paper by using quaternized alkyl tallow compounds as deinking surfactants in a washing process. Since quaternary compounds in commercial use contain IPA, or other similar soluble solvents such as hexylene glycol, the constantly recycled water used in commercial deinking can be adversely impacted by present-day compositions, since the increasing concentrations of such solvents result in process difficulties, solvent build-up and disposal problems, and eventually lead to discharge into the environment.

BRIEF DESCRIPTION OF THE DRAWING

FIG. 1 is a block diagram illustration of a commercial process for manufacturing quaternary ammonium compound of a preferred type useful in the invention, most particularly 3MHT. In Step 1, the starting material, a fatty acid triglyceride, is saponified and the fatty acids isolated. The fatty acids is reacted with ammonia to form an amide in Step 2. Saturation of the fatty alkyl radicals, if required, may be accomplished by catalytic hydrogenation of either the fatty tridyercerides prior to saponification or of the resulting fatty acids. The nitrile in Step 3 is converted by catalytic hydrogenation. Depending on the reaction conditions employed, the principal product of this catalytic hydrogenation is either a primary, secondary or tertiary amine. For instance, if the hydrogenation is carried out in the presence of high ammonia pressure, the principal product is a primary amine; alternatively, if the hydrogenation is carried out in the absence of added ammonia partial pressure, the principal product is a secondary amine. Usually the amine product is then subjected to reduction alkylation using formaldehyde or a formaldehyde equivalent in Step 5 to form a tertiary amine; the product of this reductive alkylation of a primary amine is a dimethyl alkyl amine and, of a secondary amine, a methyl dialkyl amine. Although tertiary amines will not undergo reduction alkylation, the products of the catalytic hydrogenation of nitriles to form them are usually subjected to reductive alkylation conditions to convert any primary and secondary amine impurities to tertiary amines prior to subjecting to quaternization conditions.

These tertiary amines are then diluted with a non-volatile soya diluent prior to Step 6 after the alkylating or quaternizing agent has been added in Step 5, followed by Step 6, the quaternization step. As shown in the diagram, a medium (in this case, soya oil) is incorporated before the start of Step 6 to give liquidity and proper viscosity to the reaction. The final commercially-made quaternary ammonium compound typically consists of approximately 94% pure 3MHT, shown on the left of the line of designated Final Product, together with a mixture of other "impurity" ingredients, primarily two other quaternaries. The total quaternary composition is in mixture in an approximate ratio of 9 parts quaternary ammonium compound to 1 part soya diluent, although other ratios are also possible.

Other quats can be manufactured by the process described, or by other known processes, using other diluents of the inventive type provided they have vapor pressure of about 1 mm or less at 25° C.

DESCRIPTION OF THE PREFERRED EMBODIMENTS

The invention is the discovery that certain diluents, when used in the manufacture of quaternary ammonium compounds, unexpectedly produce products which provide improved performance in various end uses, both traditional uses such as the manufacture of organoclays and detergent surfactants, and potential new uses in soap and cosmetic manufacture and as deinking chemicals for wastepaper treatment.

Diluents used in the processing to create the novel quaternary ammonium compounds include fatty acids, including oleic acid and stearic acid, soya bean oil, castor oil, safflower oil, coconut oil, mineral oils, silicones, tall oil, various isoparaffin/naphthenic alkyds and 2-ethylhexanol. Such diluents generally have a vapor pressure of 1 mm of Hg or less at 25° C. and are normally liquid at ambient temperature although solids may also be used provided that they melt and are sufficiently fluid below the quaternization reaction temperature. Particularly preferred process diluents to prepare quaternary ammonium compounds in solution according to the present invention include soya oil, safflower oil, coconut oil, tall oil, mixtures or such oils, stearic acid, oleic acid and fatty acids.

The resultant products preferably made using the above diluents in the manufacturing process, have the beneficial qualities of low volatile organic compound emission rates, high flash points, and are in liquid or solid form at room temperatures. The products of this invention comprise a mixture of a quaternary ammonium compound and the diluent used, which we call a quaternary/diluent composition.

Another approach to forming similar quaternary/diluent composition, while not preferred, is to form the quaternary ammonium compound in a conventional prior art solvent, remove the solvent by drying or evaporation, then physically combine the dried quaternary compound with the preferred new diluent in a blender, or other apparatus, heating the quaternary compound to melt it as required, and then mixing with the resultant product with the diluents of the invention.

The manufacturing process, using diluents of the present invention, of four specific quats having wide and varied commercial uses is particularly preferred; dimethyl bis [hydrogenated tallow] ammonium chloride ("2M2HT"), benzyl dimethyl hydrogenated tallow ammonium chloride ("B2MHT"), trimethyl hydrogenated tallow ammonium chloride ("3MHT") and methyl benzyl bis[hydrogenated tallow] ammonium chloride ("MB2HT"). It should be observed that the diluent fatty acids, oils or similar compounds used need not be restricted to single species or moieties having uniform chain lengths or structures. In fact, combinations or mixtures of different acceptable diluents can lead to satisfactory products, such as a mixture of 50% soya oil and 50% safflower oil. In addition, for example, a soya oil used may meet commercial specifications for virgin soya oil, while still containing other animal or vegetable oils, having soya oil of non-standard carbon chain length distribution, or containing acids having carbon groups of chain lengths and in relative percentages typical of soya oil, but which were in fact derived from fatty oils or substances other than soya oil. Further, mixtures of the inventive diluents with prior art solvents can be used if the vapor pressure of the mixture is less than about 1 mm of Hg at 25° C.

Defoaming agents may be employed during synthesis of the inventive compositions. Typical defoaming agents include various alcohols, hydrocarbons, dimethyl polysiloxane, silicone-containing compounds, alcohol alkoxylates, propoxylated alkyl amines, polyacrylates, alkyleneoxide copolymers, fatty acids, fatty acid sulfonates and blends of fatty acids and esters in hydrocarbons. Preferred defoaming agents for use in synthesizing compositions of the present invention include dimethyl polysiloxanes and silicone-containing compounds. Particularly useful defoaming agents are those composed of dimethyl polysiloxane and silica, such as Dow Corning 1400 and 1410 antifoam agents.

Quaternary ammonium compositions prepared using the above diluents can generally be employed in the same applications as those prepared using isopropyl alcohol or similar prior art solvents. Common applications would include those as an ingredient in fabric softeners, hair conditioning agents, dispersants, flocculating agents, germicides, algicides, surfactants, phase transfer catalysts, emulsifiers, antistatic agents, and as reactants for the preparation of organically-modified clays. Importantly, new uses not presently served satisfactorily by quaternary ammonium compounds, such as improved fabric softeners, deinking and cosmetics targeted to feminine consumers, can now be served. Preparation of the quaternary ammonium compound in the new diluents also eliminates the additional processing steps (vacuum or spray drying and grinding) which may be required to remove and dispose of most of the isopropyl alcohol or similar prior art solvents in certain fabric softener manufacturing processes.

Another beneficial economic aspect of the invention is cost reduction. In the making of a quaternary ammonium-modified organoclay, for example, quaternary ammonium compounds such as 2M2HT are brought into a manufacturing plant as a mixture of 83% quat/17% IPA and water, then reacted, commonly with an aqueous slurry of smectite clay, to form a smectite organoclay complex, with most of the unwanted and unneeded IPA dissolving in the waste water, with some adhering to the organoclay filter cake. Simple substitution of the compounds of this invention at the manufacturing stage will eliminate the IPA, with additional benefits resulting, since there is no IPA causing a disposal problem, nor will IPA be released to the atmosphere during organoclay filter cake drying or grinding. Furthermore, since the diluent is carried along with the organoclay, if a non-water soluble diluent is selected, the product yield per unit weight of quaternary reactant will be higher, also resulting in greater economy of usage versus the quaternary ammonium/prior art solvent situation. In addition, the diluent may be selected to provide synergistic effects to the organoclay during its usage, including effects such as improved wettability, enhanced dispersibility and reduction in moisture pick up. Synergistic effects are also possible in non-organoclay uses of the quaternary/diluent compositions of this invention, particularly in oil well drilling fluids.

The quaternary/diluent compositions of this invention can be used with wastepaper pulp aqueous systems as deinking additives. For example, a deinking organoclay may be formed in the aqueous system by adding the quaternary/diluent composition and one or more cation-exchangeable clays to the aqueous system, where these materials react to form the organoclay deinking agent. Alternatively, if the wastepaper to be treated contains cation-exchangeable clays, an organoclay deinking agent may be formed in the system without external clay addition by pulping the wastepaper to release the clay from the wastepaper and mixing in the quaternary/diluent composition to form the organoclay in situ.

Another technique involves adding a blend, composed of one or more cation exchangeable clays mixed with the quaternary/diluent composition, to the aqueous system. Upon addition of the blend to the aqueous system, the clay reacts with the quaternary to form an organoclay deinking agent. In addition the quaternary may also react with any clay contained in the wastepaper. Another technique involves adding the quaternary/diluent composition to the ink, paper sizing, or paper itself before the paper is printed, pulping the wastepaper to liberate the quaternary/diluent composition, and then separately adding a clay, to the deinking tank, so that the clay and ammonium salt(s) react to form the deinking organoclay.

Deinking processes using the present invention successfully remove water-based (flexographic) and oil-based inks as well as chemicals in adhesive-backed labels and the like ("sticky components") from wastepaper. The particular ability to collect and float flexographic ink and remove sticky components, without IPA concerns, is a notable advantage of the invention over conventional deinking techniques using prior art commercial products.

Quaternary ammonium/diluent compositions of the present invention can also be used as surfactants. Such surfactants can find use in soaps, particularly specialty soaps and liquid soaps, cosmetics and hair treatments, as well as in performing surfactant functions in wastepaper deinking processes. Dishwashing liquids and shampoos can particularly benefit from the quaternary/diluent compositions of the instant invention, especially if diluents compatible with the product media involved are selected.

Organoclays using the novel quaternary/diluent compositions of this invention may be prepared by admixing the clay, the quaternary/diluent composition and water together, preferably at temperatures from about 20° C. to 100° C., and most preferably from 35° C. to 80° C., for a period of time sufficient for the quaternary compound to react with the clay. The reaction is followed by filtering, washing, drying and grinding. The quaternary/diluent composition may be added simultaneously with process reactants, or at separate intervals. The amount of such composition added to the clay must be sufficient to impart to the clay gelling and dispersion characteristics. The amount of quaternary compounds may be equal to or in excess of the milliequivalent ratio, which is the number of milliequivalents (m.e.) of the quaternary in the organoclay per 100 grams of natural clay, 100% active clay basis. A mixture of quaternary ammonium compounds either in the same or different diluents can also be utilized.

Organophilic clay gellants using quaternary/diluent compositions according to this invention are useful as rheological additives in both non-aqueous and aqueous systems such as inks, paints, varnishes, enamels, waxes, paint-varnishes, oil base drilling fluids, lubricants and greases, polyesters, epoxy resins, adhesives, sealants, cosmetics, detergents, and the like. Such organoclays can also be used directly as deinking additives or as soil remediation chemicals. For the above uses and others, the diluent is carried along in the system, and does not contribute to the release of volatile organic compounds (VOC) to the atmosphere.

As noted above, organoclays made utilizing stearic acid as the diluent would eliminate any IPA waste product and its significant disposal cost. Certain types of organoclay manufacture require the addition of a source of sodium stearate anions to form an anion-completed product—see, e.g., U.S. Pat. No. 4,412,018. In that the sodium stearate in the prior art manufacturing process reacted with the quaternary to produce waste NaCl, an additional waste product will also be reduced or eliminated.

Organoclays made with soya diluent when used to thicken soya-based systems such as certain modern printing inks are highly dispersible and compatible with such inks. The soya diluent remains on the organoclay during its manufacture— as soya oil has little significant solubility in water at temperatures below 100° C. at atmospheric pressure. Such a product is at least as effective as prior art organoclays made with quaternary compounds dissolved in conventional solvents, and eliminates the IPA disposal problem.

Another use for the inventive organoclay/diluent use is in drilling muds. Presently manufacturers of pure or blended low-aromatic mineral oil-based drilling muds separately add organoclays to the drilling mud composites. A further organoclay use is as an agricultural carrier to facilitate the delivery of various herbicides in an enhanced manner.

Quaternary ammonium/diluent compositions of the present invention can also be used as surfactants. Such surfactants can find use in soaps, particularly specialty soaps and liquid soaps, cosmetics and hair treatments, as well as in performing surfactant functions in wastepaper deinking processes. Dishwashing liquids and shampoos can particularly benefit from the quaternary/diluent compositions of the instant invention, especially if diluents compatible with the product media involved are selected.

Quaternary/diluent compositions of the present invention are particularly useful as fabric softeners, and can be simply and efficiently added, for example, to the rinse cycle in common washing machines used at home or in "laundromats". Since there is no IPA or traditional diluent in the quaternary/diluent composition, no spray drying or evaporation steps need be employed in the manufacturing process to make detergent or softener formulations, either liquid or solid, containing these inventive compositions. Odor in particular is improved, and a wide variety of fragrances and perfumes can be utilized in combination with the novel quaternary/diluent compound. The quaternary/diluent composition can be added to polyurethane foams or to anti-static/fabric softener sheets already in common use. The diluent utilized can be selected to facilitate dispersion in the aqueous washing medium, improve the water solubility of the quaternary ammonium compound and substitute for additives (or reduce the amount used) separately added to fabric softeners, such as coconut oil or surfactants. A particularly useful quaternary composition using the instant invention for fabric softeners is 2M2HT, in light of its high anti-static behavior and ready availability.

The selection of a proper diluent in the quaternary/diluent composition can eliminate or significantly reduce many of the negative consequences of contamination by the traditional quaternary solvent. Volatile solvents can alter the degree and consistency of form, dramatically reduce viscosity, change the wettability and solubility of additives, as well as contribute to the total volatile organic content. Solvents such as diethylene glycol can present toxicity and odor problem. As a direct result of their chemical compositions, such prior art solvents can also cause film porosity, blistering and wrinkling in coatings and films. These solvents can cause surface deposits which can result in a reduction of gloss and increased haze, alteration in adhesion and non-homogenous distribution of the quaternary compound.

The following examples are given to illustrate the invention, but are not deemed to be limiting thereof.

EXAMPLE 1

Flotation deinking tests were conducted on a quaternary ammonium composition consisting of 50% 2M2HT reacted in a fatty acid diluent. The fatty acid replaced isopropyl alcohol, eliminating the need to remove that solvent after processing by an expensive drying step. An in situ generated organoclay was formed in the wastepaper by a reaction between the quaternary ammonium compound and cation-exchangeable clay contained in the wastepaper treated.

Several flotation deinking tests were performed employing the sample, composed of 2M2HT reacted in a fatty acid carrier, in the treatment of 10% water-based ink newsprint, 55% oil ink newsprint and 35% magazine European wastepaper mix. Tests included using the quat/fatty acid solvent in powder and aqueous slurry forms and introducing the sample to the pulper and dilution chest.

The quaternary/fatty acid composition was employed at a 1% loading. Wastepaper was first pulped for 20 minutes at 13% consistency in an aqueous system using a Hobart mixer. Pulping was performed with addition of 2% sodium silicate, 0.5% sodium hydroxide and 0.8% hydrogen peroxide to the aqueous pulp system. Water hardness at flotation was 250 ppm. Pulp samples for brightness evaluations were collected at 0, 6 and 12 minutes flotation. Brightness values were obtained for the top and bottom sides of the pulp by measuring the blue reflectance. Data presented in Table I shows deinked pulp brightness.

TABLE I

| Sample Description | Brightness (Top/Bottom) | | |
|---|---|---|---|
|  | 0 Min | 6 Min | 12 min |
| 1% Quat/Fatty Acid Diluent, Powder added to Pulper | 42.1/40.3 | 50.5/49.5 | 56.4/52.9 |

TABLE I-continued

| | Brightness (Top/Bottom) | | |
|---|---|---|---|
| Sample Description | 0 Min | 6 Min | 12 min |
| 1% Quat/Fatty Acid Diluent, Powder Added to Pulper - 3700 ppm Hardness in Pulper | 43.0/38.0 | 51.2/46.0 | 55.7/50.7 |
| 1% Quat/Fatty Acid Diluent, Slurry W/NAOH, added to Pulper | 38.6/31.4 | 50.8/46.6 | 55.0/51.4 |
| 1% Quat/Fatty Acid Diluent, Slurry W/NAOH, added to Dilution tank | 55.7/55.3 | 60.4/59.8 | 62.3/62.6 |

EXAMPLE 2

The flotation deinking performance of the same quaternary/diluent composition of Example 1 was evaluated (1) at various loadings and (2) using different water hardness levels at pulping. The purpose of this work was to optimize deinking processing parameters for the quaternary/fatty acid diluent composition.

The sample was introduced to the pulper as an aqueous slurry converted to the quat/sodium soap form using sodium hydroxide. Water hardness at flotation was adjusted to 200 ppm by addition of calcium chloride. The wastepaper mix used was composed of 35/35/30 water news/oil news/magazine. HunterLab brightness data is presented in Tables II and III.

TABLE II

| | Brightness (Top/Bottom) | | |
|---|---|---|---|
| % Quat/Fatty Acid Diluent | 0 Min | 6 Min | 12 min |
| 0.5% | 40.4/38.2 | 51.0/45.5 | 52.7/47.3 |
| 0.75% | 41.8/42.0 | 54.1/52.5 | 58.8/56.6 |
| 1.0% | 41.9/41.8 | 53.5/53.8 | 60.2/59.9 |
| 1.5% | 40.2/40.2 | 51.7/51.9 | 57.8/57.3 |
| 2.0% | 39.9/39.7 | 51.2/51.3 | 57.8/57.8 |

TABLE III

| | 1% Quat/Fatty Acid Diluent | | |
|---|---|---|---|
| % of Total CaCl$_2$ | Brightness (Top/Bottom) | | |
| Present in Pulper | 0 Min | 6 Min | 12 min |
| 0% | 40.5/40.6 | 50.9/50.4 | 56.5/55.1 |
| 12.6% | 41.8/39.7 | 53.3/52.2 | 57.9/56.6 |
| 25% | 40.3/41.1 | 54.3/54.1 | 60.1/59.8 |
| 50% | 42.4/41.7 | 54.4/54.4 | 61.2/59.6 |
| 100% | 41.0/41.1 | 55.7/54.5 | 61.0/60.7 |
| 100% + BRIJ 700 | 42.0/40.0 | 55.4/54.8 | 60.9/59.7 |

Data presented in Table II indicate that the highest deinked pulp brightness was obtained when the quat/fatty acid diluent composition was employed at a 1% loading. Data presented in Table III indicate that the calcium concentration at pulping has an effect on quat/fatty acid deinking performance. It appears that a level of calcium sufficient to convert all or most of the sodium soap to calcium soap should be present to minimize any negative synergism between the in situ generated organoclay and the soap collector. An insufficient level of calcium at pulping may account for the decrease in deinked pulp brightness observed in Table II for loadings of quaternary/fatty acid diluent composition greater than 1%.

EXAMPLE 3

Flotation deinking tests were conducted on a quaternary ammonium composition consisting of 50% 2M2HT which had been reacted with soybean oil. The soybean oil replaced isopropyl alcohol eliminating the need to remove isopropyl alcohol using an experience drying step. An in situ generated organoclay was formed in the wastepaper.

The 2M2HT/soybean oil sample evaluated as a flotation deinking additive versus wastepaper compared of 35/35/30 water news/oil news/magazine. Wastepaper was pulped at 4% consistency with addition of 0.16% DTPA, 1% sodium silicate, 1% sodium hydroxide, 1% hydrogen peroxide, 0.0076% Brij 700 surfactant and the deinking additive. After pulping the stock was diluted to 1% consistency and flotation deinked. Water hardness was adjusted to 200 ppm using calcium chloride. For comparison, a sample of 86.36% 2M2HT synetherized in isopropyl alcohol was also evaluated. Data presented in Table IV indicate that when compared at equal 2M2HT content, the 2M2HT/soybean oil composition provided deinked pulp brightness equal to that of the 2M2HT/IPA control.

TABLE IV

| | HunterLab Brightness (Top/Bottom) | | |
|---|---|---|---|
| Deinking Additive | 0 Min | 6 Min | 12 min |
| 1% 50%2M2HT/Soybean Oil | 44.7/45.3 | 58.0/58.4 | 62.4/62.8 |
| 0.579% 86.36% 2M2HT/IPA | 42.7/44.8 | 59.0/59.5 | 62.7/62.9 |

EXAMPLE 4

Experiments were conducted to evaluate the effects on deinking performance and product handling properties of employing additional fatty acid candidates as 2M2HT quat diluents. Studies included evaluating (1) the deinking performance of various fatty acids and (2) the deinking performance and melting points of blends composed of 2M2HT and various fatty acids. Data indicated that the fatty acid candidates themselves generally provided similar deinking performance. Blending 2M2HT with unsaturated fatty acids resulted in a significantly lower melting point compared to that obtained for blends composed of saturated acids. Varying the fatty acid diluent yielded relatively small differences in 2M2HT/fatty acid deinking performance. Compared on an equal quat basis, 2M2HT itself employed with a small amount of Brij 700 provided higher deinked pulp brightness than any of the 2M2HT/fatty acid blends.

This example describes studies conducted to evaluate the effects on deinking performance and product handling properties of employing various fatty acid candidates as quat reaction diluents. Studies included evaluating (1) the deinking performance of various fatty acids and (2) the deinking performance and melting points of blends composed of 2M2HT quat and various fatty acids.

The fatty acid candidates were evaluated for deinking performance at a 0.75% loading versus a 0/70/30 flexo news/oil news/magazine wastepaper mix. Blends of 2M2HT and the various fatty acids were melted and mixed to yield a uniform sample. The quat/fatty acid blends were evaluated for melting point and dispersibility in water. Blends which displayed sufficient dispersibility in water were evaluated for deinking performance at a 1% loading versus the 35/35/30 wastepaper mix. Both the fatty acid and quat/fatty acid samples were introduced to the pulper as aqueous slurries with the fatty acid converted to sodium soap. Water hardness was adjusted to 200 ppm by addition of calcium chloride. Data are presented in Tables V–VII.

Data presented in Table V indicate that the various fatty acids generally provide deinked pulp brightness similar to that provided by standard Serfax MT-90 soap. Two fatty acids, soya acid (Industrene 326) and tallow fatty acid (Hartaflot 7451), provided slightly higher deinked pulp brightness.

Melting point values for quat/fatty acid blends composed of (1) 62.5% 2M2HT/37.5% fatty acid and (2) 50% 2M2HT/50% fatty acid are presented in Table VI. Blending 2M2HT with unsaturated fatty acids, such as tall oil fatty acid, oleic acid and soya acid, results in a significantly lower melting point compared to that obtained for blends composed of saturated acids such as stearic acid. The ability to employ unsaturated fatty acids as 2M2HT reaction carrier provides the option to develop a product which can be more easily heated and handled as a liquid.

Dispersibility testing indicated that the 50% 2M2HT blends were much easier to disperse in water than the 62.5% 2M2HT blends. Brightness values obtained for deinked pulp treated with the 50% 2M2HT/50% fatty acid compositions are presented in Table VII. Data appear to indicate that varying the fatty acid diluent yields relatively small differences in deinked pulp brightness values. When compared on an equal quat basis, 2M2HT itself employed with a small amount of Brij 700 provided higher deinked pulp brightness than any of the quat/fatty acid blends.

TABLE V

Various fatty acids evaluated at 0.75% vs 0/70/30 wastepaper mix. 200 ppm hardness $H_2O$ fatty acid employed as an aqueous slurry with NaOH, pulp at 4% consistency with 0.16% DTPA, 1% Sodium silicate, 1% NaOH and 1% $H_2O_2$.

| Sample | Brightness (Top/Bottom) | | | % Rejects |
|---|---|---|---|---|
| | 0 Min. | 6 Min. | 12 Min. | |
| Industrene 325 (Coconut Acid) | 56.9/52.6 | 64.5/64.0 | 65.3/65.6 | 13.2 |
| Industrene 143 (Tallow Acid) | 54.5/55.9 | 63.0/62.7 | 65.8/66.6 | 21.8 |
| Industrene 105 (Oleil Acid) | — | 64.6/62.3 | 64.7/65.0 | 19.2 |
| Hystrene 3022 (30% Behenic/Arachidic) | 52.7/53.0 | 60.8/59.1 | 64.0/63.4 | 19.0 |
| Hydroxystearic Acid | 55.8/51.5 | 63.4/62.1 | 64.9/65.9 | 16.6 |
| Industrene B (Stearic Acid) | 53.5/51.9 | 60.8/60.5 | 63.7/65.1 | 28.2 |
| Industrene R (Stearic Acid) | 53.0/49.7 | 63.3/61.2 | 63.3/63.7 | 13.8 |
| Industrene 365 (Caprylic/Capric) | 52.6/52.2 | 63.1/62.8 | 64.7/63.9 | 24.1 |
| Industrene 226 (Soya Acid) | 57.7/55.6 | 65.7/66.8 | 68.1/68.3 | 21.2 |
| Unitol ACD Special (Tall Oil F.A.) | 56.2/54.8 | 63.1/61.7 | 66.2/65.0 | 14.1 |
| Hartaflot 7451 (Tallow F.A.) | 55.6/56.2 | 65.8/62.8 | 68.9/66.1 | — |
| Serfax MT-90 (Sodium Stearate) | 52.9/54.5 | 62.1/58.2 | 63.7/64.7 | 17.2 |

TABLE VI

Melting point values for 2M2HT/Fatty Acid blends.

| Sample Description | Melting Point °C. | |
|---|---|---|
| | 62.5% 2M2HT | 50% 2M2HT |
| 2M2HT/Industrene R (Stearic Acid) | 83 | 87 |
| 2M2RT/Unitol ACD Special (Tall Oil F.A.) | 48 | 45 |
| 2M2HT/Hydroxystearic Acid | 68 | 75 |
| 2M2HT/Hystrene 3022 (30% Behenic & Arachidic) | 80 | 85 |
| 2M2HT/Industrene 105 (Oleic Acid) | 60 | 58 |
| 2M2HT/Industrene B (Stearic Acid) | 83 | 90 |
| 2M2HT/Industrene 143 (Tallow Acid) | 65 | 76 |
| 2M2HT/Industrene 226 (Soya Acid) | 43 | 60 |
| 2M2HT/Industrene 325 (Coconut Acid) | 73 | 74 |
| 2M2HT/Industrene 365 (Caprylic/capric) | 42 | 42 |
| 2M2HT/Industrene R Quat Preparation | — | 80 |

TABLE VII

50/50 Blends of 2M2HT and various fatty acids. Evaluated at 1% versus 35/35/30 wastepaper mix. 200 ppm hardness $H_2O$, Quat/fatty acid employed as an aqueous slurry with NaOH. Pulp at 4% consistency with 0.16% DTPA, 1% Na silicate, 1% NaOH and 1% $H_2O_2$.

| Sample Description | Brightness (Top/Bottom) | | | % Rejects |
|---|---|---|---|---|
| | 0 Min. | 6 Min. | 12 Min. | |
| 1% 2M2HT/Industrene R Quat Preparation | 41.9/42.4 | 55.2/55.0 | 60.2/60.3 | 20.9 |
| 1% 2M2HT/Unitol ACD Special (Tall oil F.A.) | 44.1/45.6 | 55.6/56.7 | 60.2/60.5 | 24.3 |
| 1% 2M2HT/Stearic Acid | 43.0/41.9 | 51.8/49.9 | 55.8/54.0 | 11.7 |
| 1% 2M2HT/Palmitic Acid | 42.0/41.2 | 51.8/50.3 | 56.4/54.7 | 14.3 |
| 1% 2M2HT/Oleic Acid | 42.8/42.7 | 53.0/50.7 | 55.4/53.1 | 22.7 |
| 1% 2M2HT/Industrene R (Stearic Acid) | 42.1/42.4 | 51.3/52.0 | 57.0/57.7 | 18.5 |
| 0.5% 2M2HT + 1.5% Brij 700 | 46.2/47.5 | 58.6/58.8 | 63.3/63.0 | 26.6 |
| 1% 2M2HT/Industrene R Quat Preparation | 40.6/40.9 | 52.6/51.5 | 58.1/57.4 | 18.2 |
| 1% 2M2HT/Industrene 226 (Soya F.A.) | 42.3/42.0 | 52.5/50.7 | 57.0/54.9 | 22.6 |
| 1% 2M2HT/Hystrene 3022 (30% Behenic/ | 42.5/41.9 | 52.9/51.6 | 56.3/56.4 | 19.5 |

TABLE VII-continued

50/50 Blends of 2M2HT and various fatty acids.
Evaluated at 1% versus 35/35/30 wastepaper mix. 200 ppm hardness $H_2O$,
Quat/fatty acid employed as an aqueous slurry with NaOH.
Pulp at 4% consistency with 0.16% DTPA, 1% Na silicate, 1%
NaOH and 1% $H_2O_2$.

| Sample Description | Brightness (Top/Bottom) | | | % Rejects |
|---|---|---|---|---|
| | 0 Min. | 6 Min. | 12 Min. | |
| Arachidic) | | | | |
| 1% 2M2HT/Industrene 105 (Oleic Acid) | 40.7/42.3 | 53.4/52.6 | 56.9/56.2 | 21.7 |
| 1% 2M2HT/Industrene 143 (Tallow Acid) | 41.7/42.3 | 53.3/52.6 | 58.0/57.9 | 20.6 |
| 1% 2M2HT/Industrene B (Stearic Acid) | 40.0/41.0 | 51.2/51.1 | 56.1/56.8 | 15.1 |
| 1% 2M2HT/Industrene 325 (Coconut Acid) | 42.5/42.7 | 55.7/56.1 | 59.1/59.2 | 25.4 |
| 1% 2M2HT/Hydroxystearic Acid | 41.8/41.5 | 55.1/54.2 | 59.8/58.9 | 22.6 |
| 1% 2M2HT/Industrene R (Stearic Acid) | 40.2/40.1 | 51.1/50.3 | 56.2/55.7 | — |
| 1% 2M2HT/Unitol ACD Special (Tall oil F.A.) | 42.2/42.9 | 54.6/53.1 | 57.9/55.2 | 21.9 |
| 1% 2M2HT/Industrene 120 (Linseed) | 43.2/44.0 | 52.1/52.0 | 56.6/55.5 | — |
| 0.5% 2M2HT + 1.5% Brij 700 | 44.3/45.4 | 57.0/57.2 | 62.1/61.9 | 28.0 |

EXAMPLE 5

Organoclays prepared by reacting a quaternary ammonium/soya oil composition with bentonite clay were prepared and evaluated in solvent-based paint. The bentonite clay was dispersed in water (3% solids) at 65° C. and then reacted, for 30 minutes with various amounts of 80/20 2M2HT/soya oil composition, filtered and dried at 105° C., before being milled in an impact mill (centrifugal) using a 0.5mm screen. For comparison, an organoclay composed of bentonite clay reacted with conventional quaternary ammonium/IPA was also prepared. The resulting organoclays can be described as

| Organoclay No. | Composition | Theoretical | | |
|---|---|---|---|---|
| | | Quat m.e. | % o.c.* | % S.B.O.** |
| 1 | 2M2HT/Soya/Bentonite | 118.3 | 90.6 | 9.4 |
| 2 | 2M2HT/Soya/Bentonite | 99.4 | 91.5 | 8.5 |
| 3 | 2M2HT/Soya/Bentonite | 90.9 | 91.9 | 8.1 |
| 4 | 2M2HT/IPA/Bentonite | 99.4 | 100 | 0 |

*Percent organoclay by weight
**Percent soya bean oil

The organoclay compositions described above were evaluated as rheological additives in an aliphatic gloss alkyd enamel paint formulation and compared to a conventional organoclay, "BENETONE™34". The organoclays were evaluated at a loading of 7.2 pounds of active organoclay per 100 gallons of paint. Paint formulations were prepared according to the procedure detailed in Addendum 1.

Data presented in Table VIII indicate that organoclay compositions prepared using the 80/20 2M2HT/soybean oil composition provided rheological performance similar to that provided by standard organoclays made with IPA containing quaternaries.

ADDENDUM I

ALIPHATIC GLOSS ALKYD ENAMEL - AIR DRY
0.7% RHEOLOGICAL ADDITIVE

| RAW MATERIAL | POUNDS | GALLONS |
|---|---|---|
| Beckosol 10-060 Alkyd Resin Solution | 105.76 | 13.25 |
| Mineral Spirits 66/3 | 70.60 | 10.91 |
| Organoclay Rheological Additive - Active | 7.17 | 0.51 |
| Mix 3 mins. @ 3000 RPM THEN: | | |
| Methanol/Water 95/5 @ 33% Polar Activator | 2.39 | 0.36 |
| Mix 5 mins. @ 3000 RPM THEN: | | |
| KRONOS ® 2101 $TiO_2$ | 325.00 | 9.76 |
| Disperse 15 mins. @ 5000 RPM | | |
| Then letdown with: | | |
| Beckosol 10-060 | 445.90 | 55.88 |
| ZR 6% NUXTRA Drier | 10.30 | 1.43 |
| CO 6% NUXTRA Drier | 3.42 | 0.46 |
| Exkin #2 Anti-skinning Agent | 2.00 | 0.25 |
| Mineral Spirits 66/3 | 54.70 | 8.45 |
| Mix 10 mins. @ low speed | | |
| | 1027.24 | 101.26 |
| FORMULA WT/GAL 10.15 | | |
| PVC, % 18.51 | | |
| N.V. % (VOL) 52.95 | | |
| N.V. % VEH (VOL) 43.15 | | |

TABLE VIII

TEST Type: ALKYD GLOSS ENAMEL

|  | Blank | BENETONE ™ | ORGANOCLAY NUMBER | | | |
|---|---|---|---|---|---|---|
|  |  |  | 1 | 2 | 3 | 4 |
| Rheological Additive Theoretical: | None | 34 | As described | | | |
| SBO, % | — | — | 9.4 | 8.5 | 8.1 | 0 |
| O/C, % | 0 | — | 90.6 | 91.5 | 91.9 | 100 |
| Quat. M.E. % | — | — | 118.3 | 99.4 | 90.9 | 99.4 |
| Loading Level: Pounds per/hundred gallons | 0 | 7.20 | 7.94 | 7.86 | 7.84 | 7.20 |
| Polar Activator (P.A.): | — |  |  | Yes | | |
| Type P.A.: | — |  |  | MeOH/H$_2$O | | |
| Paint, F.O.G. Final | 6.5A | 6.5A | 6.5A | 6.5A | 6.5A | 6.5A |
| Stormer Visc. KU @ 77° F. | 90 | 97 | 95 | 97 | 97 | 99 |
| Brookfield Visc., cps |  |  |  |  |  |  |
| Spindle #5 10 RPM | 1100 | 2400 | 2200 | 2400 | 2500 | 2500 |
| Temp., 77° F. 100 RPM | 1100 | 1610 | 1500 | 1590 | 1670 | 1710 |
| T.I. | 1.00 | 1.49 | 1.47 | 1.51 | 1.50 | 1.46 |
| Leneta Sag, Mils | 3.5 | 5.8 | 5.8 | 5.9 | 5.9 | 6.0 |
| Gloss, |  |  |  |  |  |  |
| 60° | 85 | 84 | 86 | 85 | 84 | 84 |
| 20° | 76 | 73 | 76 | 72 | 73 | 73 |

EXAMPLE 6

This example describes the preparation of compositions composed of 2M2HT with various diluents.

The 2M2HT was a 100% active powder with no diluent. It had been obtained by taking a quaternary compound made with IPA and evaporating off the IPA. The diluents employed included LPA-170 (isoparaffin/naphthenic diluent), soybean oil and 2-ethylhexanol. Compositions composed of 50/50, 65/35 and 80/20 of 2M2HT with each diluent were prepared, an accurately weighted portion of 2M2HT was added to an accurately weighed charge of diluent and the two components were then mixed and heated until the 2M2HT was melted. The sample was then allowed to cool with mixing.

EXAMPLE 7

The samples of Example 6 were evaluated for flotation deinking performance versus wastepaper composed of 35% flexo news, 35% oil news and 30% magazine. In the deinking testing, wastepaper was pulped for 10 minutes using a Maelstrom laboratory pulper. The wastepaper was pulped at 4% consistency with 0.16% diethylenetriaminepentaacetic acid (DTPA), 1% sodium silicate, 1% sodium hydroxide, 1% hydrogen peroxide and the 2M2HT/diluent sample (percentage based on weight of wastepaper) using water (50° C.) adjusted to 200 ppm hardness with calcium chloride. A small loading of Brij 700 surfactant (1.5% based on weight of 2M2HT) was also added to enhance foaming properties. The 2M2HT/diluent composition samples were employed at loadings to yield a 2M2HT content of 0.375%. For comparison, 2M2HT dissolved in IPA was evaluated at a 0.375% loading. After pulping, the stock was diluted to 1% consistency and flotation deinked using a Denver-type laboratory flotation call. Pulp samples for brightness evaluation were collected at 0, 6 and 12 minutes flotation. HunterLab brightness data are presented in Table IX.

Data indicate that compositions composed of 2M2HT/2-ethylhexanol provided up to 1.7 units of brightness higher than pulp treated with conventional 2M2HT when compared at equal 2M2HT loading. This example demonstrates that preparing quat/diluent samples by simply blending the dried quat with the diluent using mixing and heat is an effective method of generating the quat/diluent compositions of this invention and shows improvement in performance using the quaternary/diluent compositions versus conventional technology.

TABLE IX

Pulp brightness values. Flotation deinking testing of blends composed of 2M2HT in various diluents. 35/35/30 flexo news/oil news/magazine wastepaper mix.

| Sample Description | 2M2HT Loading | Brightness (Top/Bottom) | | |
|---|---|---|---|---|
|  |  | 0 Min. | 6 Min. | 12 Min. |
| 0.375% 2M2HT | 0.375% | 43.2/44.3 | 57.4/57.3 | 61.8/61.1 |
| 0.75% 50/50 2M2HT/2-Ethylhexanol | 0.375% | 45.7/46.3 | 61.0/60.2 | 63.5/62.0 |
| 0.577% 65/35 2M2HT/2-Ethylhexanol | 0.375% | 45.0/45.3 | 59.0/57.0 | 61.9/60.0 |
| 0.469% 80/20 2M2HT/2-Ethylhexanol | 0.375% | 42.5/44.0 | 57.4/57.3 | 62.2/61.9 |

TABLE IX-continued

Pulp brightness values. Flotation deinking testing of blends composed of 2M2HT in various diluents. 35/35/30 flexo news/oil news/magazine wastepaper mix.

| Sample Description | 2M2HT Loading | Brightness (Top/Bottom) | | |
|---|---|---|---|---|
| | | 0 Min. | 6 Min. | 12 Min. |
| 0.75% 50/50 2M2HT/Soybean Oil | 0.375% | 45.0/44.6 | 56.4/54.9 | 61.2/58.9 |
| 0.577% 65/35 2M2HT/Soybean Oil | 0.375% | 42.8/44.7 | 56.7/56.2 | 60.5/60.2 |
| 0.469% 80/20 2M2HT/Soybean Oil | 0.375% | 46.0/45.3 | 56.6/54.8 | 61.5/59.4 |
| 0.75% 50/50 2M2HT/LPA-170 | 0.375% | 45.2/45.1 | 55.2/55.5 | 59.6/59.4 |
| 0.577% 65/35 2M2HT/LPA-170 | 0.375% | 43.3/44.8 | 57.0/56.6 | 60.5/60.4 |
| 0.469% 80/20 2M2HT/LPA-170 | 0.375% | 44.2/44.2 | 56.4/56.5 | 59.3/59.1 |

EXAMPLE 8

An experiment was conducted to evaluate the effectiveness of employing organoclays made with quaternary/diluent compositions of this invention as rheological additives in organic systems. Tests were conducted using a 100% mineral oil ink and involved comparing the effectiveness, using known parameters for the evaluation of rheological additives, of no additive, an additive made with a prior art IPA quaternary (2M2HT) and an additive made with a 2M2HT quaternary synthesized using a soybean oil diluent. The results are shown in Table X. Organoclays made with inventive quaternaries, without an IPA diluent and its associated problems, displayed significantly improved properties than using no rheological additive. Essentially equal misting and high shear viscosity values were found as to the prior art organoclay with an improved yield value. There was a slight but not significant lower shear value as compared with the prior art organoclay.

TABLE X

MINERAL OIL RHEOLOGY RESULTS

| Sample | 1 | 2 | 3 |
|---|---|---|---|
| Rheological Additive | None | 2M2HT IPA | 2M2HT Soya |
| % Rheological Additive | 0.00 | 1.00 | 1.00 |
| Polar Activator | N/A | NO | NO |
| Tack at 1200 RPM | 4.1 | 4.7 | 4.7 |
| Misting 1 Minute Laray @ 25° C. | Fair/Poor | Fair | Fair |
| Viscosity - Poise | 27.2 | 34.6 | 33.7 |
| Yield Value d/cm² | 50 | 213 | 258 |
| Brookfield Viscosity | | | |
| @ 30° C. - cps 20 RPM | 9625 | 25000+ | 24750 |
| 2.5 RPM | 29000 | 134000 | 120000 |
| IPA | None | Yes | None |

EXAMPLE 9

A conventional organoclay reaction was performed in a 3 liter stainless steel beaker equipped with baffles and a six blade turbine mixer. 2101.5 grams of a beneficiated bentonite clay slurry containing 2.85% clay (60 grams clay) was charged to the reactor. The clay slurry was heated to 65° C. under low agitation. Separately, 45.86 grams of Kermamine Q-9702 CLP (dimethyl distearyl ammonium chloride EMW-637) was weighted into a 100 ml beaker and heated to 65° C. The molten quaternary amine was poured into the clay slurry with agitation, and reacted for 30 minutes of 65° C. then the resulting organoclay slurry was vacuum filtered and dried at 105° C. in a forced air oven to constant weight. The dry sample was milled in a centrifugal mill for two passes through a 0.5 mm screen. This sample corresponds to Bentone™34(B34), a commercial 2M2HT bentonite made by Rheox, Inc., and was used as a control Additionally, 25.48 grams of dried Kemamine Q-9702 CLP and 4.18 grams of Conoco mineral oil LVT 200 were heated together and mixed at 65° C. to form a quat/diluent composition. A modified Bentone™34 type organoclay was then formed as above, except 1401.1 grams of bentonite slurry was used.

The modified Bentone™34 type organoclay, prepared with the Conoco LVT 200 mineral oil, was tested as a rheological additive (RA) in Formula 2-A drilling mud preparation, see Table XI, for a standard lab mix of 350 mls (conversion for one barrel of drilling mud), as follows:

Mud Preparation

In Step 1, the first five materials were added in the order shown into a Hamilton-Beach stainless steel mixing cup, then mixed for five minuets on the high speed setting of a Hamilton-Beach Mixer. After five minutes the cup was removed and place on a scale where 6 grams (ppb, 6 pound per barrel) of rheological additive is added (Step 2). The RA was mixed on the high speed setting for 15 minutes. After 15 minutes the remaining raw materials, barite and fluid loss additive were added and mixed for 10 minutes (Step 3). Total mixing time was 30 minutes.

Drilling Mud Tests

The rheological properties of the drilling mud were measured on a Fann Viscometer. Standard tests RP13B-2 of the Ammonium Petroleum Institute were used. Viscosity tests consisted of initial viscosity and viscosity after hot rolling for 16 hours at 150° F. and/or 300° F. Viscosity was measured at 77° F. on all muds (including initial and after each hot roll cycle) and at 120° F. (after hot rolling at 150° F.). For screening tests the initial and hot rolled 150° F. viscosity were tested. Plastic viscosity (PV) in centipoise, was calculated by subtracting the 300 RPM dial reading from 600 RPM dial reading. Yield Point (YP) was obtained by subtracting the PV from the 300 RPM dial reading. Three RPM, 10 second and 10 minutes gel points were also measured. Data are presented in Table XII.

SUMMARY

The modified Bentone™34 type organoclay made with the inventive quaternary/diluent displayed higher initial and retest plastic viscosity, and excellent wetting out in comparison with the prior art organoclay. The inventive diluent provided a positive synergy in reaching the improved result.

TABLE XI

14 PPG, CONOCO LVT 200 Mineral Oil 80/20 Invert Mud - Formula 2-A

| Formulation | Trade Name | Lab Formula | Step | Mix time |
|---|---|---|---|---|
| Conoco LVT 200 bbl × 350 = mls | | 200.0 mls | 1 | |
| Primary Emulsifier, lb | Invermul NT | 9.0 grams | 1 | |
| Secondary Emulsifier, lb | EZMUL NT | 2.0 grams | 1 | |
| Brine Mix, 30% Calcium Chloride in Fresh Water, mls | | 60.0 mls | 1 | |
| | | 5.0 grams | 1 | 5 min |
| Lime, lb | | 6.0 grams | 2 | 15 min |
| Rheological Additive, lb | | 325.0 grams | 3 | |
| Barite, lb | | | | |
| Fluid Loss Additive, lb | Duratone HT | 8.0 grams | 3 | 10 min |

TABLE XII

| Rheological Additive | B34 Type Control | Modified B34 Type |
|---|---|---|
| Initial @ 77° F. | | |
| Plastic Viscosity, cp | 70 | 80 |
| Yield Point, lb/100 ft² | 32 | 35 |
| 10 sec gel, lb/100 ft² | 12 | 13 |
| 10 min gel, lb/100 ft² | 20 | 23 |
| Elect. Stability, volts | | |
| Comments | Normal wetting | Excellent wetting |

Other embodiments of the invention will be apparent to those skilled in the art from consideration of the specification and practice of the invention disclosed herein. It is intended that the specification and practice of the invention disclosed herein. It is intended that the specification and examples be considered as exemplary only, with a true scope and spirit of the invention being indicated by the following claims.

What is claimed:

1. A process for making an organoclay comprising:

a) preparing an aqueous slurry of smectite clay, which slurry is at a temperature of 20° C. to 100° C.;

b) introducing into such aqueous slurry a quaternary ammonium composition comprising a quaternary ammonium compound and a diluent other than propylene glycol, hexylene glycol and diethylene glycol, where the diluent has a vapor pressure of 1 mm of mercury or less at 25° C., wherein the quaternary ammonium compound is equal to or in excess of the milliequivilant ratio of the smectite clay;

c) reacting the smectite clay with the quaternary ammonium compound thereby forming an organoclay; and d) seperating the organoclay from the slurry.

2. The process of claim 1 wherein some or all of the diluent becomes part of the formed organoclay.

3. The process of claim 1 wherein the smectite clay is beneficiated bentonite.

4. The process of claim 1 wherein the quaternary ammonium compound is selected from the group consisting of 2M2HT, B2MHT, 3MHT and MB2HT.

5. The process of claim 1 wherein the diluent is selected for the group consisting of soya bean oil, oleic acid, castor oil, stearic acid, coconut oil and tall oil.

6. The process of claim 1 wherein the diluent is stearic acid.

7. The process of claim 1 wherein a mixture of two different quaternary ammonium compounds either in the same or different diluents is utilized.

8. The process of claim 1 wherein the temperature of the slurry is from 35° C. to 80° C.

* * * * *